(12) United States Patent
Schreier et al.

(10) Patent No.: US 6,451,293 B1
(45) Date of Patent: *Sep. 17, 2002

(54) COMBINATION OF ERYTHRULOSE AND A REDUCING SUGAR WITH SELF-TANNING PROPERTIES

(75) Inventors: Thomas Schreier, Bubendorf; Roland Jermann, Laufen, both of (CH)

(73) Assignee: Pentapharm AG (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,651

(22) PCT Filed: Feb. 27, 1998

(86) PCT No.: PCT/CH98/00083

§ 371 (c)(1), (2), (4) Date: Jan. 5, 2000

(87) PCT Pub. No.: WO98/38977

PCT Pub. Date: Sep. 11, 1998

(30) Foreign Application Priority Data

Mar. 5, 1997 (CH) ................................................ 518/97

(51) Int. Cl.[7] .............................. A61K 7/42; A61K 7/44; A61K 7/00; A61K 31/70; A61N 43/04

(52) U.S. Cl. ............................ 424/59; 424/60; 424/401; 514/23; 514/937; 514/938

(58) Field of Search ............................ 424/401, 59, 60; 514/23, 937, 938

(56) References Cited

U.S. PATENT DOCUMENTS

| | | | | |
|---|---|---|---|---|
| 5,569,460 A | * | 10/1996 | Kurz et al. | 424/401 |
| 5,922,333 A | * | 7/1999 | Laughlin | 424/401 |
| 6,039,963 A | * | 3/2000 | Philippe et al. | 424/401 |
| 6,051,250 A | * | 4/2000 | Ribier et al. | 424/450 |

FOREIGN PATENT DOCUMENTS

| | | | |
|---|---|---|---|
| EP | 0 424 282 A1 | * | 4/1991 |
| WO | WO-95/22960 A1 | * | 8/1995 |

\* cited by examiner

*Primary Examiner*—Jose' G. Dees
*Assistant Examiner*—Marina Lamm
(74) *Attorney, Agent, or Firm*—Pennie & Edmonds LLP

(57) ABSTRACT

The invention relates to an active ingredient combination containing erythrulose and a further reducing sugar with self-tanning properties, for example, dihydroxyacetone, which combination is used for artificially tanning the skin. Compared with compounds containing, for example, only dihydroxyacetone, said active ingredient combination and cosmetic compounds based thereon result in an even and longer-lasting colouring of the skin and prevent skin dehydration and uneven flaking.

26 Claims, 1 Drawing Sheet

COMBINATION OF ERYTHRULOSE AND A REDUCING SUGAR WITH SELF-TANNING PROPERTIES

This application is a 371 of PCT/CH98/00083 filed Feb. 27, 1998.

The present invention relates to a combination of erythrulose in D- or L-form or as the racemate and at least one additional reducing sugar having self-tanning properties and cosmetic compositions containing these for the artificial tanning of the skin. The cosmetic compositions bring about a more even and longer-lasting coloration of the skin and prevent the drying out and uneven peeling thereof compared to known compositions that, for example, contain dihydroxyacetone alone.

Hydroxyketones and hydroxyaldehydes are known active substances for self-tanning agents. The active substances generally processed into creams react with free amino groups of the Stratum corneum and result in brownish-coloured pigments that are bound to proteins of the Stratum corneum. This conversion of reducing sugars with amino acids, peptides or proteins, known as the Maillard reaction, leads to compounds having a carbonyl function that polymerise to brown melanoids.

The hitherto most frequently used active substance is dihydroxyacetone (hereinafter referred to as "DHA"). The fast tanning active substance (4–7 hours) does, however, have some disadvantages. The skin colour achieved is yellowish-brown, which produces an unnatural colour, particularly in pale skin. In addition, the tan is irregular and soon pales again because the top-most layers of the epidermis are quickly shed.

It has now been found that a combination of DHA—or another reducing sugar having similar properties—with erythrulose does not display the above disadvantages. This may be attributed to the fact that erythrulose dyes the skin more slowly (the colour takes about 20–24 hours to develop) and less intensively, but instead also penetrates lower layers of the Stratum corneum where it is also able to react with the free amino groups. This not only results in more even tanning, but also in a retarded effect, with the result that the tan lasts longer. Moreover the skin becomes less dried out than, for example, with DHA alone. The synergistic effect, that will subsequently also be shown with reference to examples, of the active substance combination erythrulose/other reducing sugars, such as for example DHA, was not predictable.

Figure 1:
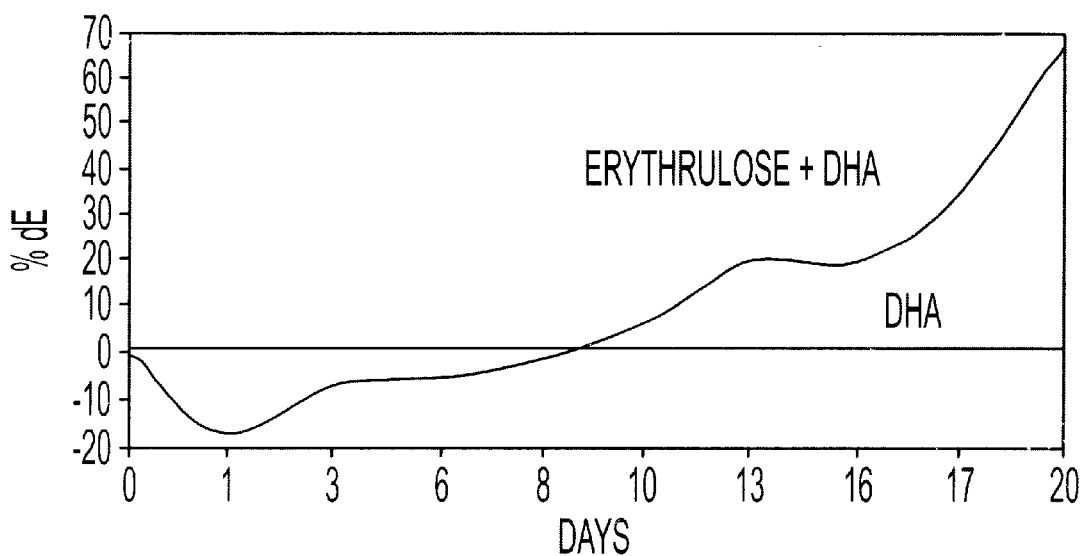
FIG. 1 shows the different influence of a formulation containing DHA alone and a formulation containing erythrulose and DHA on skin color intensity.

Erythrulose alone can also be used as sole active substance for slightly tanning day creams. The advantage of erythrulose compared to other reducing sugars having a self-tanning effect, in particular DHA, lies in the fact that the skin is tanned more evenly and without forming undesirable streaks.

Erythrulose is a C4-ketosugar of the general structural formula 1,3,4-trihydroxy-butan-2-one that occurs naturally or that can be prepared chemically or biotechnologically in a manner known per se. Erythrulose can be used in D- or L-form or also as the racemate. DHA is a C3-ketosugar having the general structural formula 1,3-dihydroxy-propan-2-one that can be prepared in a manner known per se.

Other reducing sugars having self-tanning properties that can be used in combination with erythrulose are, for example, glucose, xylose, fructose, reose, ribose, arabinose, allose, tallose, altrose, mannose, galactose, lactose, sucrose, erythrose and glyceraldehyde.

The active substance combination contains a ratio of erythrulose to reducing sugar of about 10:1 to 1:10, advantageously about ca. 1:1 to 1:3; 1:2 being particularly preferred.

A cosmetic formulation uses about 1–5% erythrulose and about 1–15% reducing sugar, advantageously about 1.5% erythrulose and 3.5% reducing sugar.

The stability of erythrulose with a reducing sugar in a cosmetic formulation depends on many factors. The active substance combination can be used in O/W (e.g. cream or lotion) and also W/O emulsions and other types of cosmetic formulations (e.g. multiple emulsions such as O/W/O or W/O/W emulsions, gels, ointments, aerosols). The stability of the active substances can be quantitatively determined using chromatography. To do this, the emulsion is diluted, membrane filtered and analysed using HPLC.

The oily phase in emulsions can, for example, contain hydrocarbon oils such as paraffin oil or mineral oils, waxes such as beeswax or paraffin wax, silicon oils such as cyclomethicone or dimethicone, fatty alcohols such as stearyl alcohol or cetyl alcohol, natural oils such as jojoba oil, sesame oil or sunflower oil, fatty acid esters such as isopropyl myristate or glyceryl stearate or mono-, di- or triglycerides such as for example caprylic/capric acid triglyceride.

In the case of oil-in-water emulsions, the oil phase advantageously comprises 5–45% by weight, in particular about 10–30% by weight of the total formulation.

As emulsifiers for oil-in-water and water-in-oil emulsions it is possible to use emulsifiers known per se, such as silicons, sesquioleates, sorbitan esters, alkoxylated sorbitan and fatty acid esters, alkoxylated mono-, di- and triglycerides, optionally alkoxylated polymers such as crosspolymers of ethylene oxide and propylene oxide, optionally alkoxylated fatty alcohols, fatty acids, esters of natural oil derivatives, ethers such as polyethylene glycol(n)stearyl ether and polyethylene cetyl(n)stearyl ether.

The emulsifiers are advantageously used in amounts of 0.1–15% by weight related to the total formulation.

The formulations of the invention may also contain additional auxiliary substances such as for example stabilisers such as mannitol or cyclodextrin, moisturizers such as glycerol and propylene glycol, thickening agents such as acrylic acid polymers or cellulose derivatives, anti-oxidants such as tocopheryl acetate, pH-correcting agents such as sodium phosphate, film-forming agents such as PVP, preservatives such as phenoxyethanol and paraben, colorants, fragrances, softeners, antiseptics, bactericides, vitamins, pigments, propellants as well as other compounds that are cosmetically or medicinally desirable. Examples of other compounds of this nature are set out in the CTFA International Cosmetic Ingredient Dictionary, $6^{th}$ edition, The Cosmetic, Toiletry and Fragrance Association, Inc., Washington D.C., 1995.

Lipophilic systems are quite generally more suitable for cosmetic formulations of self-tanning agents. Tanning can be accelerated and the colour intensity significantly increased by adding penetration enhancers. The following have proved to be particularly suitable as penetration enhancers: dimethicone, cyclomethicone, propylene glycol dipelargonate, propylene glycol or ethoxy diglycol. The colour intensity measured was up to 55% higher with formulations containing penetration enhancers as compared to the basic formulation without penetration enhancers.

Synthetic oils such as Miglyol 812, isopropyl palmitate and silicon oils and natural lipids such as jojoba oil and sesame oil are particularly compatible with the active substance combination and are therefore particularly preferred.

Gels can also be used as formulation base for the compositions of the invention. Carbomers, cellulose derivatives and other gellants can be contained as gel-forming substances.

Insofar as the cosmetic formulation is intended to provide both a self-tanning effect and also protection against solar radiation, it is also possible to add to the formulation one or several sunscreens, such as for example octyl methoxycinnamate and/or butyl methoxydibenzoylmethane.

When processing the active substances into cosmetic formulations, care must be taken to ensure that the active substances are only added at lower temperatures of about <40° C. and that the pH value 5 is not exceeded in the cosmetic formulations, this being easily achieved through buffering.

The active substance combination of the invention, or the cosmetic formulations based thereon, can be applied to the human skin in conventional manner.

The invention will now be explained in greater detail with reference to examples, the percentages in each case constituting % by weight.

EXAMPLE 1

A self-tanning body lotion is prepared by mixing together an oily phase composed of 12.00% Cutina GMS (glyceryl stearate), 1.50% Eumulgin B1 (Ceteareth-12), 1.50% Eumulgin B2 (Ceteareth-20), 4.00% isopropyl myristate, 7.00% paraffin oil and 4.00% Miglyol 812 (caprylic/capric acid triglyceride) and heating to 70° C. and mixing together an aqueous phase composed of 51.20% demineralised water, 0.50% Phenonip and 3.00% glycerol and heating to 75° C. The aqueous phase is then added to the oily phase with stirring and cooled to 50° C., homogenised and cooling continued to 30° C. and an additional aqueous phase composed of 10.00% demineralised water, 1.50% erythrulose and 3.50% dihydroxyacetone is then added to the mixture and stirred until cold. This produces a body lotion that is agreeable to use.

EXAMPLE 2

A self-tanning white lotion is prepared by mixing together an oily phase composed of 1.50% Arlatone 983 S (PEG-5 glyceryl stearate), 2.20% Arlatone 985 (PEG-5 glyceryl stearate), 1.50% Brij 76 (Steareth-10), 5.00% Miglyol 812 (caprylic/capric acid triglyceride), 4.00% paraffin oil and 1.00% silicon oil AK 500 (dimethicone) and heating to 70° C. and mixing together an aqueous phase composed of 59.30% demineralised water, 0.50% Phenonip and 10.00% propylene glycol and heating to 75° C. The aqueous phase is then added to the oily phase with stirring and cooled to 50° C., homogenised and cooling continued to 30° C. and an additional aqueous phase composed of 10.00% demineralised water, 1.50% erythrulose and 3.50% dihydroxyacetone is then added to the mixture and stirred until cold. This produces a lotion that is agreeable to use.

EXAMPLE 3

A self-tanning white lotion is prepared by analogy with Example 2, except that 3.00% erythrulose and 2.00% DHA are used. As in Example 2, this produces a lotion that is agreeable to use.

EXAMPLE 4

A self-tanning cream is prepared by mixing together an oily phase composed of 1.00% Cremophor A6 (Ceteareth 6 and stearyl alcohol), 1.00% Cremophor A25 (Ceteareth 25), 3.00% Cutina GMS (glyceryl stearate), 10.00% paraffin oil, 5.00% jojoba oil and 1.00% cetyl alcohol and heating to 70° C. and mixing together an aqueous phase composed of 48.50% demineralised water, 0.50% Phenonip and 5.00% propylene glycol and heating to 75° C. The aqueous phase is then added to the oily phase with stirring and cooled to 50° C., homogenised and cooling continued to 30° C. and an additional aqueous phase composed of 15.00% demineralised water, 5.00% cyclodextrin, 1.50% erythrulose and 3.50% dihydroxyacetone is then added to the mixture and stirred until cold. This produces a cream that is agreeable to use.

EXAMPLE 5

A self-tanning O/W cream with sunscreen is prepared by mixing together an oily phase composed of 5.00% of a mixture of glyceryl stearate and PEG-100-stearate, 1.00% cetyl alcohol, 2.00% stearic acid, 4.00% dimethicone, 2.00% cyclomethicone, 3.00% caprylic/capric acid triglyceride, 1.00% jojoba oil, 4.00% isopropyl palmitate, 2.00% octyl methoxycinnamate and 1.00% butyl methoxydibenzoylmethane, heating to 75° C. and adding an aqueous phase heated to 80° C. composed of 51.20% demineralised water, 0.50% Phenonip, 6.00% propylene glycol and 2.00% glycerol and stirring thoroughly. The emulsion obtained is cooled to 50° C. and homogenised. At 30° C. an additional aqueous phase composed of 10.00% demineralised water, 1.50% erythrulose and 3.50% dihydroxyacetone is then added and stirred thoroughly.

EXAMPLE 6

A self-tanning W/o/W cream is prepared by preparing an aqueous solution of 2.00% Poloxamer, 0.10% Phenonip, 16.02% demineralised water, 0.38% magnesium sulfate heptahydrate, 1.40% xanthan gum, 0.10% Phenonip, and 20.00% demineralised water and adding 60.00% of a previously prepared W/O emulsion consisting of an oily phase containing 3.30% of a mixture of sorbitan ester and polyglycerol ester, 3.00% polyglycerol ester, 15.00% isohexadecan, 14.00% caprylic/capric acid triglyceride and an aqueous phase with 55.50% demineralised water, 0.20% Phenonip, 0.70% magnesium sulfate heptahydrate, 2.50% erythrulose and 5.80% DHA and homogenising.

EXAMPLE 7

A self-tanning gel is prepared by mixing together 1.00% PVM (copolymer composed of vinyl chloride and vinylmethyl ether)/MA-decadien crosspolymer, 0.50% Phenonip and 83.50% demineralised water, adjusting the pH to 3.7 with sodium hydroxide solution and adding 15% of a mixture of 66.70% demineralised water, 10.00% erythrulose and 23.30% DHA.

EXAMPLE 8

A self-tanning day cream is prepared by mixing together 5.00% Arlacel 165 (glyceryl stearate, PEG-100-stearate), 1.00% cetyl alcohol, 2.00% stearic acid, 4.00% Dow Corning 200 silicon (dimethicone polymethylsiloxan), 2.00% Belsil CM 020 (cyclomethicone), 3.00% Miglyol 812 (caprylic/capric acid triglyceride), 1.00% jojoba oil, 4.00% isopropyl palmitate, 2.00% Parsol MCX (octyl methoxycinnamate) and 1.00% butyl methoxydibenzoylmethane and heating this oily phase to 70° C. In parallel thereto, 57.20% deionised water, 0.50% Phenonip, 6.00% propylene glycol and 2.00% glycerol are mixed and this aqueous phase is heated to 75° C. The aqueous phase is then added to the oily phase with stirring and the mixture cooled to 50° C., homogenised and cooled further to 30° C. A mixture composed of 5.00% deionised water and 4.00% erythrulose is then added and stirred until cold, whereupon the entire mixture is then reacted with 0.30% Belamie 0/241710.

This produces a day cream that with daily application gives the skin a slightly brownish coloration and healthy appearance. The sunscreens also protect the skin from the effects of harmful UV radiation.

EXAMPLE 9

To investigate the synergistic effect of erythrulose and DHA on the tanning of the skin a tanning study was conducted to compare an O1W lotion containing 1.5% erythrulose and 3.5% DHA according to Example 1 with a lotion containing DHA.

Fields measuring 10×14 cm were marked on the back of 4 male and 4 female subjects. The subjects were neither allowed to sunbathe nor to visit a solarium during the entire period of the study.

Before the measurements, the subjects were acclimatised for 15 min in a skin laboratory at 26–28° C. and 40–50% air humidity. Immediately after measuring the initial value on day 0, the marked test fields were treated with 0.3 ml of the appropriate lotion with light rubbing in. This procedure was repeated on the following 9 days. No more lotion was applied after the $10^{th}$ day.

From the first day to the $20^{th}$ day the colour changes as well as the skin moisture were in each case measured immediately before the next application. The skin moisture was measured using the CM 820 Corneometer (Courage and Khazaka). The skin colour was measured using the Minolta CR 300 Chromameter.

The skin colour was quantified using the "CIE L*a*b* colour system". This defines the colours in a three-dimensional colour co-ordinate system. The a* value corresponds to the red-green axis, the b* value to the yellow-blue axis and the L* value to the pale-dark axis. The smaller the L* value, the darker the colour. The difference between two measuring points in this three-dimensional colour co-ordinate system can be calculated from the absolute values using the following formula:

$$\Delta E(CIEL^*a^*b^*) = \sqrt{(L_1^* - L_2^*)^2 + (a_1^* - a_2^*)^2 + (b_1^* - b_2^*)^2}$$

The value calculated using this formula is a parameter for the colour change of the skin.

FIG. 1 shows the different influence of the two formulations tested on the colour intensity. The diagram shows the percentage colour difference of the combination of erythrulose and DHA compared to DHA. The use of DHA alone colours the skin faster during the first few days. However, from the $10^{th}$ day on, the intensity of coloration of the combination erythrulose and DHA was greater. After application was discontinued, the difference in the intensity of coloration of the combination of erythrulose and DHA compared to DHA alone was increasingly more marked because of the delayed decrease in coloration. This shows that erythrulose produces a visible retarded effect.

The skin coloration achieved with erythrulose and DHA does not show any streak formation and the skin shows no peeling due to greater drying out.

Figure 2:
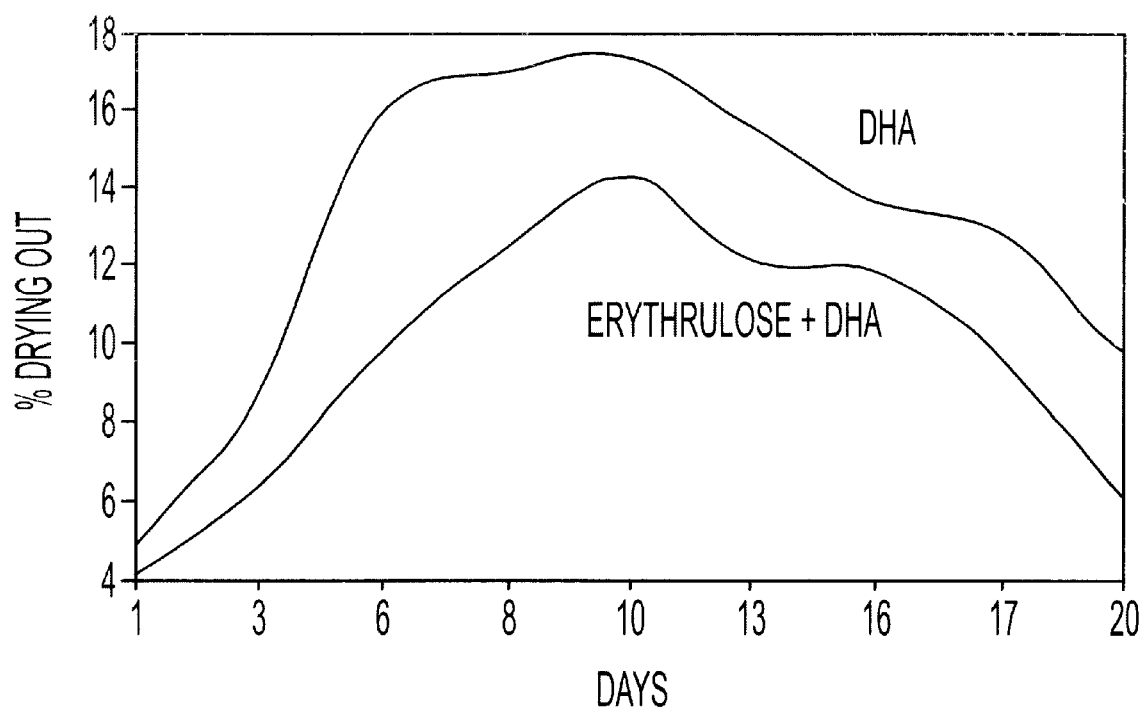
FIG. 2 shows the different influence of a formulation containing DHA alone and a formulation containing erythrulose and DHA on the drying-out of the skin.

Measurements show that the use of erythrulose and DHA in an O/W emulsion causes up to 30% less drying out of the skin (FIG. 2). The skin feels less dry. When using the combination of erythrulose and DHA in comparison to the DHA emulsion, the test subjects did not feel any skin tightness.

What is claimed is:

1. An active substance combination for the artificial tanning of the skin comprising a combination of erythrulose in D- or L-form or as a racemate and an additional reducing sugar having self-tanning properties.

2. An active substance combination according to claim 1, wherein the ratio between erythrulose and the additional reducing sugar having self-tanning properties lies between 10:1 to 1:10.

3. An active substance combination according to claim 1, wherein the additional reducing sugar having self-tanning properties is DHA.

4. A cosmetic formulation comprising an active substance combination according to claim 1, wherein about 1–5% erythrulose and about 1–15% of an additional reducing sugar having self-tanning properties are used.

5. A cosmetic formulation comprising an active substance combination according to claim 1 wherein the additional reducing sugar having self-tanning properties is DRA.

6. A cosmetic formulation according to claim 4 being in the form of an O/W emulsion.

7. A cosmetic formulation according to claim 6, wherein the oily phase amounts to 5–45% by weight of the total formulation.

8. A cosmetic formulation according to claim 4 further comprising at least one penetration enhancer.

9. A cosmetic formulation according to claim 4 further comprising at least one compound acting as sunscreen.

10. A process for the topical use of an active substance combination according to claim 1, comprising topically applying to the skin the active substance combination at an amount sufficient to effect artificial tanning of the skin.

11. An active substance combination according to claim 2, wherein the additional reducing sugar having self-tanning properties is DHA.

12. A cosmetic formulation comprising an active substance combination according to claim 2, wherein about 1–5% erythrulose and about 1–15% of an additional reducing sugar having self-tanning properties are used.

13. A cosmetic formulation comprising an active substance combination according to claim 12, wherein about 1.5% erythrulose and about 3.5% of an additional reducing sugar having self-tanning properties are used.

14. A cosmetic formulation comprising an active substance combination according to claim 2, wherein the additional reducing sugar having self-tanning properties is DHA.

15. A cosmetic formulation according to claim 5 being in the form of an O/W emulsion.

16. A cosmetic formulation according to claim 5 further comprising at least one penetration enhancer.

17. A cosmetic formulation according to claim 5, further comprising at least one compound acting as sunscreen.

18. A cosmetic formulation according to claim 15, wherein the oily phase amounts to about 5–45% by weight of the total formulation.

19. A process for the topical use of a cosmetic formulation according to claim 4, comprising topically applying to the skin the cosmetic formulation at an amount sufficient to effect artificial tanning of the skin.

20. A process for the topical use of a cosmetic formulation according to claim 12, comprising topically applying to the skin the cosmetic formulation an amount sufficient to effect artificial tanning of the skin.

21. An active substance combination according to claim 2, wherein the ratio between erythrulose and the additional reducing sugar having self-tanning properties lies between about 1:1 to about 1:3.

22. An active substance combination according to claim 21, wherein the ratio between erythulose and the additional reducing sugar having self-tanning properties is about 1:2.

23. A cosmetic formulation containing an active substance combination according to claim 4, wherein about 1.5% erythrulose and about 3.5% of an additional reducing sugar having self-tanning properties are used.

24. A cosmetic formulation according to claim 7, wherein the oily phase amounts to about 10–30% by weight of the total formulation.

25. A cosmetic formulation according to claim 17, wherein the compound acting as sunscreen is octyl methoxycinnamate or butyl methoxydibenzoylmethane, or a mixture thereof.

26. A cosmetic formulation according to claim 18, wherein the oily phase amounts to about 10–30% by weight of the total formulation.

* * * * *